United States Patent [19]

Detwiler et al.

[11] Patent Number: 4,505,801

[45] Date of Patent: Mar. 19, 1985

[54] OVERCOAT COMPOSITIONS AND ION-SELECTIVE ELECTRODES FOR IONIC ANALYTE DETERMINATIONS

[75] Inventors: Richard L. Detwiler, Rochester; Brooke P. Schlegel, Canandaigua; Thomas R. Kissel, Rochester, all of N.Y.

[73] Assignee: Eastman Kodak Company, Rochester, N.Y.

[21] Appl. No.: 569,695

[22] Filed: Jan. 10, 1984

[51] Int. Cl.$^3$ ............................................. G01N 27/30
[52] U.S. Cl. ..................... 204/418; 204/416; 252/312; 436/175; 524/714; 524/755; 524/757
[58] Field of Search ............... 204/418, 416; 252/312; 524/714, 755, 757; 210/643; 436/175

[56] References Cited

U.S. PATENT DOCUMENTS

| | | | |
|---|---|---|---|
| Re. 27,888 | 1/1974 | Li ................................. | 210/643 X |
| Re. 28,002 | 4/1974 | Li ................................. | 210/643 X |
| Re. 30,125 | 10/1979 | Li et al. ......................... | 210/643 X |
| 4,214,968 | 7/1980 | Battaglia et al. ................ | 204/418 |
| 4,272,328 | 6/1981 | Kim et al. ....................... | 204/1 T |
| 4,303,408 | 12/1981 | Kim et al. ....................... | 436/175 |

*Primary Examiner*—G. L. Kaplan
*Attorney, Agent, or Firm*—J. Lanny Tucker

[57] ABSTRACT

An overcoat composition for use in ion-selective electrodes comprises: (a) a discontinuous liquid phase comprising an oleophilic solvent dispersed within a continuous phase comprising a hydrophilic binder; (b) a complexing agent useful for extracting oleophilic anions; (c) a buffer which provides a pH in the range of from about 7.5 to about 9.5 under conditions of use; and (d) a nucleating agent. This overcoat composition is particularly useful in ion-selective electrodes for determination of $CO_2$.

10 Claims, No Drawings

OVERCOAT COMPOSITIONS AND ION-SELECTIVE ELECTRODES FOR IONIC ANALYTE DETERMINATIONS

FIELD OF THE INVENTION

This invention relates to analytical elements for potentiometric determination of ion concentrations in aqueous liquids, such as body fluids. In particular, it relates to dry-operative ion-selective electrodes for determination of $CO_2$ in such liquids.

BACKGROUND OF THE INVENTION

Control of the acid-base balance in the human body is maintained by intricate renal and pulmonary mechanisms. A disturbance in this balance is generally accompanied by changes in the electrolyte composition of the blood. Therefore, several analyses are necessary to ascertain the acid-base status. One important analysis performed in the clinical laboratory is the determination of the concentration of carbon dioxide in the blood.

Carbon dioxide dissolved in blood is in equilibrium between the interior of red blood cells and the plasma and also within the plasma. It undergoes the following reaction:

$$CO_2 + H_2O \rightleftharpoons H_2CO_3 \rightleftharpoons HCO_3^- + H^+ \rightleftharpoons 2H^+ + CO_3^=$$

The interrelationship between total $CO_2$, $HCO_3^-$, dissolved $CO_2$ and pH (not taking into account the insignificant amounts of $CO_3^=$ and carbamino compounds) is described in the literature (see *Fundamentals of Clinical Chemistry*, Norbert W. Tietz, ed., second edition, W. B. Saunders, Co., Philadelphia, Pa., p. 893, 1976). With the aid of the Henderson-Hasselbach equation described in the literature, one can calculate pH, $pCO_2$, total $CO_2$ and $HCO_3^-$ knowing any two of these. $pCO_3$ is the partial pressure of $CO_2$ gas in a hypothetical gas phase with which the blood would be in equilibrium.

Potentiometric determination of the total $CO_2$ has been performed using a carbonate ion-selective electrode. This requires the measurement of the pH of the sample to be tested or the fixing of the pH of the sample by the addition of a buffered solution prior to testing, such as described in U.S. Pat. No. 4,131,428. This procedure, however, requires a separate step in addition to the measurement by the ion-selective electrode. Moreover, the measurement of $CO_2$ by carbonate ion-selective electrodes is further adversely affected by interferences by such ions as gentisate, salicylate and p-aminosalicylate. Therefore, an ion-selective electrode for the determination of $CO_2$ in a liquid sample which does not require an additional step and which has a minimum of interference from gentisate, salicylate and p-aminosalicylate has been sought in the art.

Significant advances relating to ion-selective electrodes, and particularly, electrodes for the determination of $CO_2$ are described in U.S. Pat. Nos. 4,214,968 (issued July 29, 1980 to Battaglia et al); 4,272,328 (issued June 9, 1981 to Kim et al) and 4,303,408 (issued Dec. 1, 1981 to Kim et al). In the first reference, improved dry-operative ion-selective electrodes are described. In the second reference, an ionophore-containing membrane layer is positioned between an electrolyte zone and an adjacent buffer zone containing a buffer sufficient to provide a pH in the range of from about 7.5 to about 9.5 when wetted with liquid. The third patent relates to the use of an interferent-removing zone in ion-selective electrodes to reduce the undesirable effects of salicylate and other interferents.

The search continues, however, for ion-selective electrodes which have even better precision in $CO_2$ measurements and which exhibit reduced sensitivity to potential interferents, such as salicylate, particularly at high interferent levels in small children.

Another problem that can arise in using planar dry-operative ion-selective electrodes is that the outermost layer of the electrode, at least for certain assays, may be so hydrophobic, due to the chemistry, that drops of liquid to be assayed resist contact with the layer. That is, electrodes analyzing for $CO_2$ and for other potentiometric ions advantageously feature a buffer overcoat or an emulsion overcoat. A useful buffer overcoat for $CO_2$ electrodes is described, e.g., in the aforesaid U.S. Pat. No. 4,272,328. This overcoat has a high contact angle with aqueous liquids such as serum in view of its chemical components, and particularly the polymeric binder. It is nevertheless advantageous because it provides a buffer needed to convert $CO_2$ to its ionic forms and acts to remove certain interferents.

Examples of useful emulsion overcoats can be found in aforesaid U.S. Pat. No. 4,303,408. These overcoats also tend to have a high surface contact angle with aqueous liquids, and yet are advantageous because they help to remove interferents. Alternatively, the emulsion overcoat is often conveniently combined with the aforementioned buffer overcoat, again producing a high contact angle.

When the aqueous sample drops resist contact with the electrode, the liquid tends to move up the side of the tip of the metering device or pipette, a condition known as "perfusion." Not only does this prevent proper spotting of the electrode at this time, it also interferes with the metering of successive drops. The problem then has been, prior to this invention, to find a method for reducing the contact angle of the liquid with the outermost electrode layer, particularly when such outermost layer is one of the aforesaid overcoats.

It is known, of course, that surfactants are commonly added to liquids to reduce their contact angle. However, optimum clinical analyses procedures are those that require no additional liquids to be added to the patient sample prior to analysis. If the surfactant is added to the web, it has not been clear which surfactant, if any, will outperform the others. Furthermore, if large amounts of surfactant are needed, there has been the concern that such large amounts may in themselves act as an interferent to the web chemistry. That is, although surfactants are commonly added to electrode layers as an aid to the coating of that layer, these have generally been added in amounts that are so small, e.g., 0.15 g/m², that (a) they are not present in amounts that could be interferents, and (b) are ineffective to overcome the hydrophobic nature of the layer.

SUMMARY OF THE INVENTION

In accordance with this invention, it has been found that certain ion-selective compositions and electrodes containing same exhibit high selectivity for carbonate ions over potential interfering ions, e.g. salicylate, particularly at high salicylate concentrations. These electrodes also exhibit unexpectedly improved precision in $CO_2$ determinations. Further, it has been found that with the electrodes of this invention, the problem with perfusion has been considerably reduced.

In accordance with one aspect of this invention, an ion-selective composition comprises:
 a. a discontinuous liquid phase comprising an oleophilic solvent dispersed within a continuous phase comprising a hydrophilic binder;
 b. a complexing agent useful for extracting oleophilic anions;
 c. a buffer which provides a pH in the range of from about 7.5 to about 9.5 under conditions of use; and
 d. a nucleating agent.

This invention also provides an ion-selective electrode for determination of $CO_2$ in an aqueous liquid, said electrode comprising a support having thereon, in sequence, a metal/metal halide zone, an electrolyte zone, a membrane zone containing an ionophore, and an overcoat zone,
 said overcoat zone comprising:
 a. a discontinuous liquid phase comprising an oleophilic solvent dispersed within a continuous phase comprising a hydrophilic binder;
 b. a complexing agent useful for extracting oleophilic anions;
 c. a buffer which provides a pH in the range of from about 7.5 to about 9.5 under conditions of use; and
 d. a nucleating agent.

In another aspect of the invention, there is provided an ion-selective electrode useful for analyzing the activity of potentiometric ions in an aqueous sample, the electrode comprising (a) an overcoat comprising an emulsion or buffer layer effective to remove interferents and including a binder that is a terpolymer of N-isopropylacrylamide, and (b) an ion-selective membrane underneath the layer, the overcoat including a surfactant. The electrode is improved in that the surfactant is a nonionic octylphenoxy polyethoxyethanol surfactant having at least 30 ethoxy groups, in an amount effective to reduce the contact angle of the layer when the sample is applied, compared to the electrode lacking the nonionic surfactant in the overcoat.

Thus, it is an advantageous feature of the invention that a surfactant has been discovered that is effective to reduce the contact angle of the outermost electrode layer with aqueous liquids without interfering with the analysis, even when added in large amounts.

DESCRIPTION OF THE PREFERRED EMBODIMENTS

The ion-selective compositions and electrodes containing same of this invention are prepared, in general, according to the procedures and including the layer components generally described in U.S. Pat. Nos. 4,214,968; 4,272,328; and 4,303,408, noted hereinabove, the disclosures of which are incorporated herein in their entirety. They can be used to determine the amount of $CO_2$ in biological fluids, e.g. blood serum.

To solve the perfusion problem mentioned in the "Background of the Invention," a nonionic octylphenoxy polyethoxyethanol surfactant with at least 30 ethoxy groups is added to the emulsion or buffer overcoat, in amounts effective to reduce the contact angle. Preferably the contact angle is reduced to an amount no larger than about 50°, and most preferably no larger than about 40° (measured immediately after spotting with patient sample). The amount of surfactant to make a useful reduction in contact angle is at least about 1.0 g/m², and most preferably about 1.5 g/m². Surprisingly, this large amount does not act in any way adversely to the analysis chemistry.

A preferred example of such a surfactant is Triton X-305 ™ available from Rohm & Haas (Philadelphia, Pa.), which has exactly 30 ethoxy groups. Similar useful surfactants with a larger number of ethoxy groups include Triton X-405 ™, also from Rohm & Haas.

Surprisingly, other nonionic surfactants have been found to be ineffective in these large amounts. Included here are the nonylphenoxypolyglycidol surfactants obtained from Olin Mathieson as "Olin 10G ™," and the surfactants that are the same as Triton X-305 ™ except that only 9.5 ethoxy groups are present, namely Triton X-100 ™. Part of the problem with these surfactants is that they may cause penetration of the ion-selective membrane.

A representative ion-selective electrode for $CO_2$ determination is illustrated as follows:

| | | |
|---|---|---|
| Overcoat Layer | Poly(2-hydroxyethyl acrylate-co-acrylic acid, sodium salt-co-N—isopropylacrylamide) (36:23:41 weight ratio) binder | 16.7 g/m² |
| | Tris(hydroxymethyl)aminomethane hydrogen fluoride and tris(hydroxymethyl)-aminomethane buffers | 26.2 g/m² |
| | Trioctylpropylammonium chloride complexing agent | 3 g/m² |
| | Diisodecyl phthalate oleophilic solvent | 10 g/m² |
| | Triton X-305 ™ nonionic surfactant | 1.5 g/m² |
| | Calcium silicate nucleating agent | 0.9 g/m² |
| Membrane Layer | Poly(vinyl acetate-co-vinyl chloride) (90:10 weight ratio) binder | 6 g/m² |
| | Poly(vinyl chloride-co-vinyl acetate-co-vinyl alcohol) (91:3:6 weight ratio) binder | 4 g/m² |
| | Diisodecyl phthalate oleophilic solvent | 6.2 g/m² |
| | Decyltrifluoroacetophenone ionophore | 5 g/m² |
| | Trioctylpropylammonium chloride | 2.9 g/m² |
| | DC 510 ™ surfactant | 0.008 g/m² |
| Electrolyte Layer | Deionized gelatin | 5 g/m² |
| | Biocide | 0.008 g/m² |
| | NaCl | 1.9 g/m² |
| | KCl | 0.6 g/m² |
| | Surfactant 10G ™ nonionic surfactant | 0.03 g/m² |
| | Glycerol | 0.4 g/m² |
| Electrode | AgCl Layer | 0.1–2 g/m² |
| | Ag° | 0.5–10 g/m² |
| | Support | |

The invention has been described in detail with particular reference to preferred embodiments thereof, but it will be understood that variations and modifications can be effected within the spirit and scope of the invention.

We claim:

1. An overcoat composition useful in ion-selective electrodes, said composition comprising:
 a. a discontinuous liquid phase comprising an oleophilic solvent dispersed within a continuous phase comprising a hydrophilic binder;
 b. a complexing agent useful for extracting oleophilic anions;

c. a buffer which provides a pH in the range of from about 7.5 to about 9.5 under conditions of use; and d. a nucleating agent.

2. The composition of claim 1 comprising a nonionic octylphenoxy polyethoxyethanol surfactant having at least 30 ethoxy groups.

3. An ion-selective electrode for determination of $CO_2$ in an aqueous liquid, said electrode comprising a support having thereon, in sequence, a metal/metal halide reference electrode zone, an electrolyte zone, a membrane zone containing an ionophore, and an overcoat zone, said overcoat zone comprising:

a. a discontinuous liquid phase comprising an oleophilic solvent dispersed within a continuous phase comprising a hydrophilic binder;

b. a complexing agent useful for extracting oleophilic anions;

c. a buffer which provides a pH in the range of from about 7.5 to about 9.5 under conditions of use; and d. a nucleating agent.

4. The ion-selective electrode of claim 3 wherein said oleophilic solvent is diisodecyl phthalate.

5. The ion-selective electrode of claim 3 wherein said complexing agent is trioctylpropylammonium chloride.

6. The ion-selective electrode of claim 3 wherein said nucleating agent is calcium silicate.

7. In an ion-selective electrode useful for analyzing the activity of potentiometric ions in an aqueous sample, the electrode comprising (a) an overcoat comprising an emulsion or buffer layer effective to remove interferents and including a binder that is a terpolymer of N-isopropylacrylamide, and (b) an ion-selective membrane underneath said layer, said overcoat including a surfactant;

the improvement wherein the surfactant is a nonionic octylphenoxy polyethoxyethanol surfactant having at least 30 ethoxy groups, in an amount effective to reduce the contact angle of said layer when said sample is applied, compared to said electrode lacking said nonionic surfactant in said overcoat.

8. In an ion-selective electrode useful for analyzing the activity of potentiometric ions in an aqueous sample, the electrode comprising (a) an overcoat comprising an emulsion or buffer layer effective to remove interferents and including a binder that is a terpolymer of N-isopropylacrylamide, and (b) an ion-selective membrane underneath said layer, said overcoat including a surfactant;

the improvement wherein the surfactant is a nonionic octylphenoxy polyethoxyethanol surfactant having 30 ethoxy groups, in an amount of at least $1.0 \, g/m^2$.

9. An ion-selective electrode for determination of $CO_2$ in an aqueous liquid, said electrode comprising a support having thereon, in sequence, a metal/metal halide reference electrode, an electrolyte layer, a membrane layer containing an ionophore, and an overcoat layer, said overcoat layer comprising:

a. diisodecyl phthalate at a coverage of at least about 10 grams per square meter dispersed in poly(2-hydroxyethyl acrylate-co-acrylic acid, sodium salt-co-N-isopropylacrylamide) present at a coverage of at least about 16 grams per square meter;

b. trioctylpropylammonium chloride at a coverage of at least about 3 grams per square meter;

c. a buffer which provides a pH in the range of from about 7.5 to about 9.5 under conditions of use;

d. a nonionic octylphenoxy polyethoxyethanol surfactant having 30 ethoxy groups at a coverage of at least about 1.5 grams per square meter; and e. calcium silicate at a coverage of at least about 0.9 grams per square meter.

10. The ion-selective electrode of claim 9 wherein said ionophore is decyltrifluoroacetophenone.

* * * * *